US00PP07844P

United States Patent [19]

Kientzler

[11] Patent Number: Plant 7,844

[45] Date of Patent: Mar. 31, 1992

[54] NEW GUINEA IMPATIENS PLANT NAMED EPIA

[75] Inventor: Ludwig Kientzler, Gensingen, Fed. Rep. of Germany

[73] Assignee: Paul Ecke Ranch, Inc., Encinitas, Calif.

[21] Appl. No.: 577,135

[22] Filed: Sep. 5, 1990

[51] Int. Cl.[5] ..... A01H 5/00

[52] U.S. Cl. ..... Plt./68

[58] Field of Search ..... Plt./68, 87.6

[56] References Cited

U.S. PATENT DOCUMENTS

P.P. 6,685 3/1989 Kientzler ..... Plt. 68

P.P. 6,728 4/1989 Kientzler ..... Plt. 68

*Primary Examiner*—Howard J. Locker

*Attorney, Agent, or Firm*—Foley & Lardner

[57] ABSTRACT

An Impatiens plant named Epia having large, brilliant orange-red flowers, green leaves with yellow variegation appearing on older leaves near basal end of mid-vein, early and floriferous flowering, long-lasting flowers, and compact growth habit with excellent self-branching.

1 Drawing Sheet

The present invention relates to a new and distinctive cultivar of impatiens plant known by the cultivar name Epia, botanically known as Impatiens, and commercially known as New Guinea impatiens.

Epia was developed by the applicant through a controlled breeding program in Gensingen, Federal Republic of Germany. The male or pollen parent was identified by the cultivar designation B 590, and the female or seed parent was identified by the cultivar designation B 2870. Epia was discovered and selected as one flowering plant within the progeny of the cross by the applicant in a controlled environment in Gensingen, Federal Republic of Germany.

The first act of asexual reproduction of Epia was accomplished when terminal or stem cuttings were taken from the initial selection by applicant in a controlled environment in Gensingen, Federal Republic of Germany. Horticultural examination of selected plants of Epia has demonstrated that the combination of characteristics as herein disclosed for Epia are firmly fixed and are retained through successive generations of asexual reproduction.

Epia has not been observed under all possible environmental conditions. The phenotype may vary significantly with variations in environment such as temperature, light intensity, soil conditions, nutrient feeding, and day length.

The following characteristics distinguish the new impatiens from both its parent varieties and other cultivated impatiens of this type known and used in the floriculture industry within the knowledge of applicant:

1. Large, brilliant orange-red flowers.
2. Green leaves, with yellow variegation appearing on older leaves along the basal end of the mid-vein.
3. The plant flowers early and is very floriferous, with the flowers being long-lasting.
4. Compact growth habit with excellent branching.

The accompanying colored photograph illustrates in perspective view the overall appearance of this cultivar, with colors being as true as it is reasonably possible to obtain in a colored reproduction of this type.

The following is a detailed description of Epia based on plants produced under commercial practice in Encinitas, Calif. Unrooted cuttings were rooted under intermittent mist, and the plants subsequently transplanted to 15 cm. pots. Flowering commenced in November 1989. Cuttings were taken from these established plants in January 1990, rooted and planted in 10 cm. pots. After 5–6 more weeks the plants were nicely proportioned for 10 cm. pots, and data was collected. Most of the data which follows was collected between Apr. 1–15, 1990 in Encinitas, Calif. The measurements and description of foliage were taken from fully expanded leaves.

Color references are made to the Royal Horticultural Society Colour Chart except where general terms of ordinary dictionary significance are used. Color chart correlations were made under indirect natural light conditions, with the leaves and flowers being compared to the R.H.S. colour chart on a north exposure.

Epia is similar in flower color to the cultivar Aurore, disclosed in applicant's U.S. Plant Pat. No. 6,685, and Marumba, disclosed in U.S. Plant Pat. No. 7,372. However, Epia is distinguished from both of these cultivars by its more compact growth habit and more self-branching. Epia further distinguishes from Marumba by its variegated foliage.

Parentage: Seedling from cross pollination, of male and female parents B 590 and B 2870, respectively, being unknown at this time.

Propagation:

*Type cutting.*—Tip cutting. Stems 2–3 cm. long will develop to 4–5 cm. after 21 days in propagation.

*Time to initiate roots.*—8–10 days at 23° C. Nicely developed root mass in 18–21 days.

*Rooting habit.*—Numerous, fibrous adventitious roots from the stem.

PLANT DESCRIPTION

Form: Symmetrical, bush shaped, flowering herb, with self-branching characteristics giving the plant a full appearance.

Habit of growth: Self-branching, compact habit, producing whorls of leaves and flowers on branched stems. Growth is indeterminate and flowering is continuous.

Size: When grown as single plants in 10 cm pots with the plants not being pinched, plants in full flower are 20–22 cm in height (including the pot), 21–23 cm in width spread, and have an average number of 7 strong branches.

Foliage description: Leaves are simple. Lower leaves on stem are opposite. Higher leaves in whorls of 3–5, but predominately 5.

*Leaf shape.*—Ovate.

*Leaf blade size.*—7–8 cm. × 3–3.5 cm.

*Leaf margin.*—Finely ciliated.

*Leaf texture.*—Somewhat undulant. (a) Upper surface: Glabrous. (b) Under surface: Glabrous.

*Leaf color.*—Dark green, with yellow variegation along the basal end of mid-vein on older leaves. The yellow variegation is not visible in the color photograph. (a) Upper surface: Green, darker than R.H.S. 147A; yellow variegation near R.H.S. 11A. (b) Under surface: Grayed-purple near R.H.S. 183B.

*Venation.*—Pinnate with red mid-vein.

FLOWERING DESCRIPTION

Flowering habit: Very floriferous, flowering continuously. Flowers develop progressively around the whorl of leaves, taking 5–7 days from buds which show color to bloom. Flowers are single and large, lasting for 2–3 weeks.

Natural flowering season: Flowering is indeterminate and occurs throughout the year. Quantity of flowers increases with increasing light intensity and duration.

Flower buds: Ellipsoidal and covered with 5 sepals. A reddish, approximately 4 cm long spur originates from the base of the major sepal. Two smaller sepals are on either side of the spurred sepal and two additional, rudimentary sepals are fused to back of the top petal.

Flowers borne: Singly, on pedicels 3–4 cm. long and reddish in color.

Quantity of flowers: Floriferous, with one to mostly two flowers per leaf occurring progressively around the whorl of leaves so that tight buds to mature blooms are visible at the same time in large numbers.

Petals:

*Number of petals.*—Five (5).

*Shape.*—Top petal heart shaped with wide base, all other petals heart shaped with pointed base. All petals overlap.

*Color.*—Upper surface: Brilliant orange-red, more intense than R.H.S. 33A. Under surface: Orange, near R.H.S. 33B.

*Size of flowers.*—4.5–5 cm. diameter.

Reproductive organs:

*Stamens.*—Five (5), with the lower stamen being shorter than the other stamens. Stamens are united in an asymmetrical tube surrounding the ovary.

*Anthers.*—Hooded, cream fused with red.

*Pollen.*—Cream color.

*Stigma.*—Five pointed star, creamy white.

*Styles.*—Very short, reddish in color.

*Ovary.*—5 celled, 3–4 mm. long until fertilized, green in color.

I claim:

1. A new and distinct cultivar of Impatiens plant named Epia, as illustrated and described.

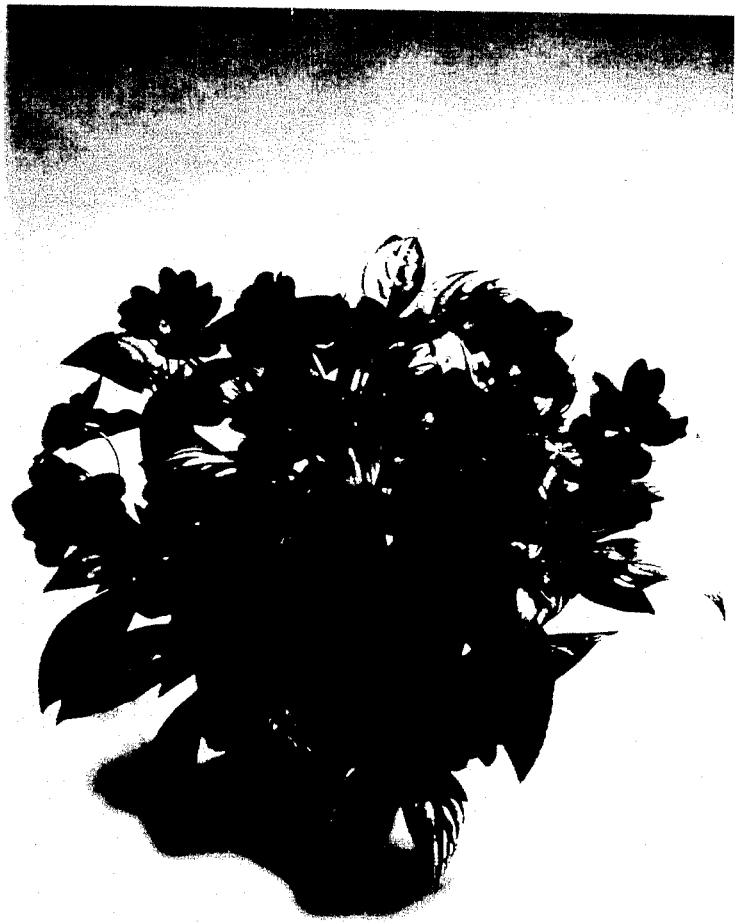

* * * * *